(12) United States Patent
Lee et al.

(10) Patent No.: US 11,291,656 B2
(45) Date of Patent: *Apr. 5, 2022

(54) PRAMIPEXOLE TRANSDERMAL DELIVERY SYSTEM AND USES THEREOF

(71) Applicant: TRANSWELL BIOTECH CO., LTD., HsinChu (TW)

(72) Inventors: Catherine Lee, West Linn, OR (US); Taijung Wu, Taoyuan (TW)

(73) Assignee: TRANSWELL BIOTECH CO., LTD., Hsinchu (TW)

( * ) Notice: Subject to any disclaimer, the term of this patent is extended or adjusted under 35 U.S.C. 154(b) by 0 days.

This patent is subject to a terminal disclaimer.

(21) Appl. No.: 16/900,140

(22) Filed: Jun. 12, 2020

(65) Prior Publication Data

US 2020/0368209 A1 Nov. 26, 2020

Related U.S. Application Data

(63) Continuation of application No. 15/384,286, filed on Dec. 19, 2016, now Pat. No. 10,729,679, which is a continuation of application No. PCT/US2016/055866, filed on Oct. 7, 2016.

(51) Int. Cl.
| | |
|---|---|
| *A61K 31/428* | (2006.01) |
| *A61K 9/70* | (2006.01) |
| *A61K 47/10* | (2017.01) |
| *A61K 47/14* | (2017.01) |
| *A61M 37/00* | (2006.01) |

(52) U.S. Cl.
CPC .......... *A61K 31/428* (2013.01); *A61K 9/7061* (2013.01); *A61K 47/10* (2013.01); *A61K 47/14* (2013.01); *A61M 37/00* (2013.01)

(58) Field of Classification Search
CPC .... A61K 9/7061; A61K 31/428; A61K 47/10; A61K 47/14; A61P 25/16; A61P 25/14
See application file for complete search history.

(56) References Cited

U.S. PATENT DOCUMENTS

| 5,008,110 A | 4/1991 | Benecke |
|---|---|---|
| 2007/0225379 A1 | 9/2007 | Carrara |
| 2016/0113908 A1 | 4/2016 | Deshmukh |
| 2018/0028465 A1 | 2/2018 | Schurad |

FOREIGN PATENT DOCUMENTS

| CN | 103432104 A | 12/2013 |
|---|---|---|
| CN | 103610666 | 3/2014 |
| EP | 2177217 | 4/2010 |
| WO | WO 2013150032 | 4/2010 |
| WO | PCT/JP2011/001381 | 9/2011 |
| WO | WO 2014188329 A2 | 11/2014 |

OTHER PUBLICATIONS

U.S. Appl. No. 14/489,252, Jan. 1, 2015, Dario Norberto R. Carrara.
U.S. Appl. No. 13/473,724, Sep. 6, 2006, Frank Teobald et al.
U.S. Appl. No. 12/302,065, Oct. 15, 2009, Michael Horstmann et al.
U.S. Appl. No. 11/731,493, Feb. 3, 2015, Eran Blaugrund et al.
U.S. Appl. No. 13/000,892, Nov. 26, 2013, Ronald Aung-Din.
U.S. Appl. No. 11/957,157, Aug. 27, 2013, Michale E. Bozik et al.
U.S. Appl. No. 13/204,351, May 21, 2013, Michale E. Bozik et al.
U.S. Appl. No. 13/570,593, May 21, 2013, Michale E. Bozik et al.
U.S. Appl. No. 14/893,020, Apr. 28, 2016, Abhijit Mukund Deshmukh et al.
U.S. Appl. No. 11/770,269, Sep. 25, 2008, Arnaud Grenier et al.
U.S. Appl. No. 11/770,194, Jul. 24, 2008, Arnaud Grenier et al.
U.S. Appl. No. 14/245,398, Dec. 23, 2014, David Kanios.
U.S. Appl. No. 13/715,276, Oct. 21, 2014, David Kanios et al.
U.S. Appl. No. 12/7981,126, Apr. 28, 2014, David Kanios et al.
U.S. Appl. No. 13/488,195, Jun. 3, 2014, Guy Dipierro et al.
U.S. Appl. No. 10/975,043, Apr. 22, 2014, David Kanios et al.
U.S. Appl. No. 13/229,007, Jan. 21, 2014, David Kanios.
U.S. Appl. No. 13/198,405, Jan. 21, 2014, David Kanios et al.
U.S. Appl. No. 11/245,084, Jan. 1, 2013, David Kanios et al.
U.S. Appl. No. 12/979,978, Oct. 2, 2012, Viet Nguyen.
U.S. Appl. No. 11/245,106, Aug. 21, 2012, Viet Nguyen.
U.S. Appl. No. 10/484,876, Mar. 18, 2008, Cornelia Beier et al.
U.S. Appl. No. 10/362,182, Aug. 21, 2007, Reinhard Horowski et al.
U.S. Appl. No. 10/433,373, May 22, 2007, Cornelia Beier et al.
U.S. Appl. No. 10/428,016, Aug. 16, 2005, Kathryn Traci-Jane Klose et al.
U.S. Appl. No. 10/086,457, Oct. 28, 2003, David Kanios.
U.S. Appl. No. 09/586,906, Oct. 15, 2002, Sylvia Rossi-Montero et al.
U.S. Appl. No. 09/318,121, Apr. 24, 2001, Jesus Miranda.
U.S. Appl. No. 07/610,870, Dec. 5, 1992, Bernd Zierenberg.
U.S. Appl. No. 11/256,189, Oct. 19, 2006, David Houze et al.
U.S. Appl. No. 09/768,831, May 16, 2002, David Houze et al.
U.S. Appl. No. 08/178,558, Aug. 12, 1997, Jesus Miranda et al.
U.S. Appl. No. 11/883,672, Jun. 12, 2008, Aida et al.
U.S. Appl. No. 12/571,509, Apr. 8, 2010, Tang et al.
Henkel Corporation "Duro-Tak and Gelva transdermal pressure sensitive adhesives" cached google and dated 2013, http://na.henkel-adhesives.com/us/content_data/330922_11061_LT5343_Product_selector2_Web863600.pdf (Year: 2013).
PU Tingting et al. Dev. of a Prolonged-Release Pramipexole Transderal Patch. Epub https://www.aaps.org/PharmSciTech/.AAPS PharmSciTech. May 31, 2016. AAPS. United States.

*Primary Examiner* — Erin E Hirt
(74) *Attorney, Agent, or Firm* — Leason Ellis LLP

(57) ABSTRACT

A pramipexole transdermal patch for treatment of neurological disorders including Parkinson's disease that may be administered on a daily basis. The pramipexole transdermal patch of the present invention preferably comprises a drug-containing layer that comprises pramipexole or a pharmaceutically acceptable salt thereof at 2% to about 15% by weight of the drug-containing layer and at least two acrylic polymers wherein each polymer may further comprise carboxyl and/or hydroxyl functional groups. The pramipexole transdermal patch of the present invention may further comprise two or more permeation enhancers with combined pramipexole solubility of great than 50 mg/mL.

9 Claims, 2 Drawing Sheets

PRAMIPEXOLE TRANSDERMAL DELIVERY SYSTEM AND USES THEREOF

CROSS-REFERENCE TO RELATED APPLICATION(S)

The present application is a continuation application of U.S. application Ser. No. 15/384,286, filed Dec. 19, 2016, which is a continuation application of and claims priority to PCT/US2016/55866 filed Oct. 7, 2016, entitled "Pramipexole Transdermal Delivery System and Uses Thereof." all of which are hereby incorporated by reference herein in their entireties.

FIELD OF THE INVENTION

The present invention relates to a pramipexole transdermal patch. More specifically the present invention relates to a pramipexole transdermal patch for daily administration, method of making and use thereof.

BACKGROUND OF THE INVENTION

Parkinson's disease (PD) is a chronic and progressive neurodegenerative disorder with symptoms such as resting tremor, rigidity, bradykinesia and postural instability. These symptoms are largely caused by progressive loss of dopaminergic neurons in the substantia nigra compacta, which ultimately reduces dopaminergic input to the striatum and other brain regions.[1] Medications for treating PD symptoms are typically orally administered in the form of tablets or capsules containing active pharmaceutical ingredient levodopa or pramipexole amongst others such as ropinirole, amantadine, catechol-omethyl transferase (COMT) inhibitors, rasagiline, rotigotine and biperidine.

[1] Ferrer I, Martinez A, Blanco R, Dalfo E, Carmona M (2011) Neuropathology of sporadic Parkinson disease before the appearance of parkinsonism: preclinical Parkinson disease. J Neural Transm 118: 821-839

Levodopa (L-dihydroxyphenylalanine or L-dopa) is a dopamine precursor which is administered with carbidopa, a dopa-decarboxylase (DDC) inhibitor, so that the levodopa is decarboxylated substantially within the central nervous system. However, with extended use of levodopa, fluctuations in motor control can occur with increasing frequency and severity, eventually disabling the patient.

Pramipexole is a member of the class of drugs known as dopamine agonists that may be administered concurrently with levodopa to help alleviate the fluctuations in motor control. Dopamine agonists (DAs) are synthetic agents which directly stimulate dopamine receptors and are used either in monotherapy for the treatment of the motor symptoms of PD in the early stage of the disease or in the later phase of the disease to lessen motor complications associated with levodopa therapy.

Although PD medications are typically in the form of tablets and capsules, transdermal patches offer an alternative form of administration. Specifically, compared to tablets and capsules, transdermal patches provide reduced dosing frequency, prolonged therapeutic duration, avoidance of gastrointestinal absorption as well as hepatic first-pass metabolism, minimized fluctuation in plasma drug concentrations, noninvasive administration with advantages over the oral route of administration, easy termination of drug administration by simply removing the patch from the skin and improved patient compliance.[2,3]

[2] Prausnitz M, Langer R., Transdermal drug delivery, Nat Biotechnology. 2008 November; 26(11): 1261-1268
[3] Gaikwad A., Transdermal drug delivery system: Formulation aspects and evaluation, Comprehensive Journal of Pharmaceutical Sciences. February 2013, Vol. 1(1), pp. 1-10

With respect to improved patient compliance, the transdermal patch is particularly beneficial to PD patients in comparison to tablets or capsules. The reason is that PD tablets and capsules require multiple daily doses in contrast with the transdermal patch which is capable of providing prolonged therapeutic duration with just one single application, simplifying dosing regimen and, thereby, facilitating patient compliance. In addition, a patient can easily forget whether he or she has already taken a capsule or tablet whereas, in contrast, a patient can easily tell whether a new transdermal patch has been applied, making it easier for a patient to follow required dosing regimen. Dosing regimen compliance in the patients with PD is particularly important since PD is a progressive, neurological disease that requires lifelong treatment. The simplified drug regimen would substantially improve the quality of life of the PD patients as well as their caregivers.

Published patent applications CN 103432104, Tingting Pu et al. AAPS PharmaSciTech 2016 published online May 31, 2016 and US 2016/0113908, the disclosures of which are incorporated herein by reference, each disclose pramipexole transdermal patches applied for therapeutic duration over multiple days use, the former two references describing use over a five to seven day period per patch application while the latter US publication describes a therapeutic use ranging from at least two days through one hundred sixty eight hours (seven days) per patch. This publication also references in paragraph 0073 that the acrylic base adhesive is preferably based on acrylates lacking a carboxylic acid functional group.

Although week-long pramipexole transdermal patches provide substantially simpler dosaging regimen in comparison to tablets and capsules, the prolonged therapeutic duration can itself create challenges. For example, a week-long pramipexole transdermal patch requires high drug loading that increases potential risks with respect to toxicity and dose dumping. In addition, by design, the high drug loading and prolonged therapeutic duration dictate that the patches do not allow moisture to pass through since moisture enhances the likelihood of pramipexole crystallization. A transdermal patch on a patient's skin that does not permit for moisture pass through for a days at a time may cause skin irritation that may become severe.[4] Moreover, from a practical point of view, requiring a transdermal patch to be applied to the skin for days at a time may also be an obstacle in the way of a patient's other daily needs such as showers or baths. Therefore, a pramipexole transdermal patch with therapeutic duration of about 24 hours, or a daily pramipexole transdermal patch, may provide advantages for administering pramipexole not only as compared to tablets and capsules but also compared to transdermal patches of week-long duration.

[4] Paude K., Milewski M., Swadley C., Brogden N., Ghosh P. and Stinchcomb A., Challenges and opportunities in dermal/transdermal delivery, NIH Public Access; 2010 Jul. 1 (1): 109-131

There exists a commercially available transdermal patch for daily administration that provides a dopamine agonist for treating PD called Neupro® transdermal patch that contains rotigotine as the active pharmaceutical ingredient. However, it has been reported that rotigontine presents a higher risk of hypotension and somnolence in comparison with pramipexole.[5] In addition, U.S. Pat. No. 7,344,733 refers to transdermal pramipexole and ropintrole patches and references product deficiencies of a pramipexole patch described in EP-B1-0 428 038 in terms of very rapid decomposition of the active ingredient accompanied by discoloration and the pramipexole crystallization. The '733 patent describes the use of acrylate monomer adhesives alone or polymerized with functional monomers. However, none of the listed acrylates use adhesive admixtures contain both a functional hydroxyl and carboxylic acid group.

[5] Etminan M, Gill S and Samil A., Comparison of the risk of adverse events with pramipexole and ropinirole in patients with Parkinson's disease: a meta-analysis., Drug Saf, 2003; 26(6):439-44

Therefore, it is an object of the invention to provide a pramipexole transdermal patch for daily administration with minimal pramipexole blood concentration fluctuations. It is another object of the invention to provide a pramipexole transdermal patch with high flux and low pramipexole crystallization.

SUMMARY OF THE INVENTION

The present invention provides a transdermal patch for treating Parkinson's disease comprising a drug-containing layer, a backing layer and a protective layer wherein the drug-containing layer comprises pramipexole or a pharmaceutically acceptable salt thereof and two or more polymers wherein at least two of the polymers each further comprises a carboxyl functional group and/or a hydroxyl functional group. In some embodiments, the pramipexole or its pharmaceutically acceptable salt thereof comprises pramipexole free-base, pramipexole dihydrochloride or dexpramipexole. In another embodiment, the pramipexole or its pharmaceutically acceptable salt thereof is in an amount from about 2% to about 15% by weight of the drug-containing layer. In yet another embodiment, the at least two polymers comprises two acrylate-based polymers. In some embodiments, the acrylate-based polymers comprise a carboxyl group-containing acrylic-based polymer and a hydroxyl group-containing acrylic-based polymer. In other embodiments, the carboxyl group-containing acrylic-based polymer is sourced from a solution of cross-linked acrylates copolymer comprising acrylic acid and 2-ethylhexyl acrylate. In yet other embodiments, the hydroxyl group-containing acrylic-based polymer is sourced from a polymer solution of acrylates copolymer comprising 2-hydroxyethyl acrylate or from a polymer solution of acrylates copolymer comprising vinyl acetate and 2-hydroxyethyl acrylate. In some embodiments, the carboxyl group-containing acrylic-based polymer and the hydroxyl group-containing acrylic-based polymer are in a ratio of from about 2:1 to about 1:2 by weight.

In some embodiments, the drug-containing layer further comprises a combination of two or more permeation enhancers. In other embodiments, the combination of two or more permeation enhancers has pramipexole solubility of above about 50 mg/mL. In yet other embodiments, the two or more permeation enhancers comprise fatty acids, fatty alcohols, solvent and/or surfactants. In some embodiments, the two or more permeation enhancers comprise aliphatic alcohols, fatty acids having chain of 8 to 20 carbons, fatty acid esters, alcohol amines, polyhydric alcohol alkyl ethers, polyoxyethylene alkyl ethers, glycerides, middle-chain fatty acid esters of polyhydric alcohols having chain of 8-20 carbon atoms, alkyl esters having chain of 1-6 carbon atoms, acylated amino acids, pyrrolidone, pyrrolidone derivatives, ethoxylated fatty alcohols, surfactants or a combination thereof.

In some embodiments, the transdermal patch of the present invention provides flux rate of more than about 0.8 µg/cm² hr and less than about 10 µg/cm² hr for up to about 40 hours. In other embodiments, lag time for the transdermal patch of the present invention is less than about 8 hours.

The present invention also provides for a method for treating a neurological disorder comprising the step of administering the transdermal patch of the present invention to a human subject in need thereof through the human's skin for a period of about 24 hours. In other embodiments, the total delivered amount of pramipexole is from about 0.2 mg to about 10 mg daily. In yet other embodiments, the neurological disorders comprise Parkinson's disease, Restless Leg Syndrome, migraine headaches, or ALS

DETAILED DESCRIPTION OF THE INVENTION

Figure 1:
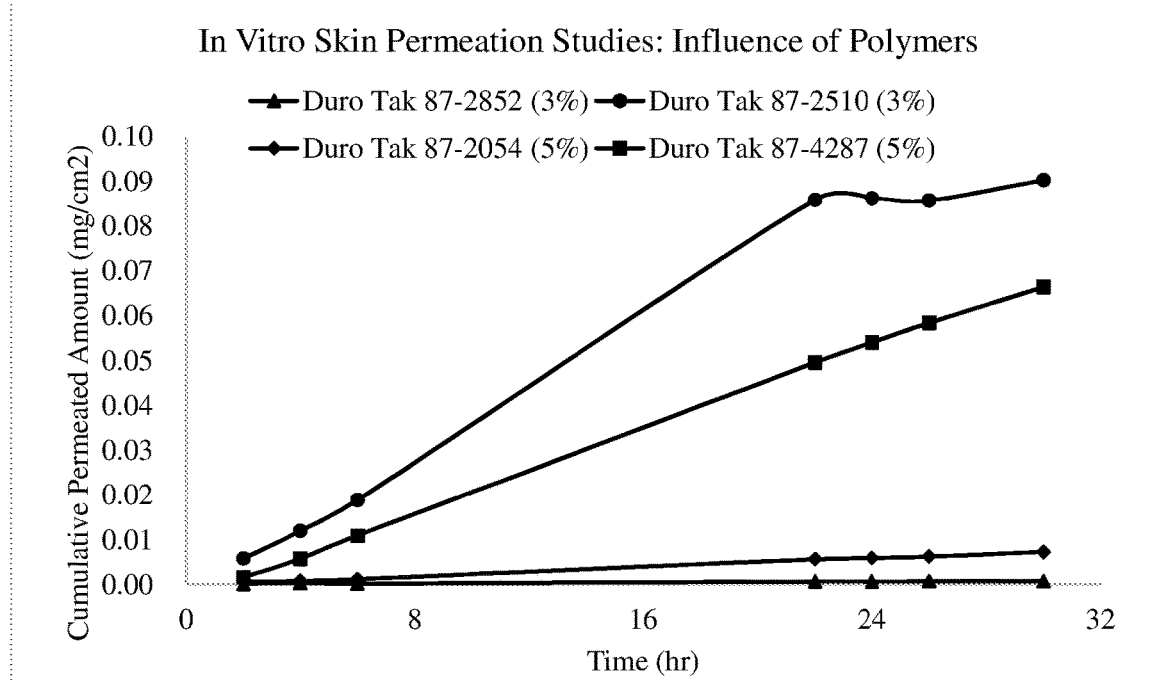
FIG. 1 illustrate in vitro cumulative permeated pramipexole in mg/cm² versus time in hours for 30 hours for transdermal patches made from Duro Tak 87-2852, Duro Tak 87-2510, Duro Tak 87-2054 and Duro Tak 87-4287, respectively.

As used in this specification and in claims which follow, the singular forms "a", "an" and "the" include plural referents unless the context clearly indicates otherwise. Thus, for example, reference to "an ingredient" includes mixtures of ingredients, reference to "an active pharmaceutical agent" includes more than one active pharmaceutical agent, and the like.

The terms "active agent", "pharmacologically active agent" and "drug" are used interchangeably herein to refer to a chemical material or compound that includes a desired pharmacological, physiological effect and include agents that are therapeutically effective. The terms also encompass pharmaceutically acceptable, pharmacologically active derivatives and analogs of those active agents specifically mentioned herein, including, but not limited to, salts, esters, amides, prodrugs, active metabolites, inclusion complexes, enantiomers S(−) or R(+) (see U.S. Pat. No. 8,445,474, the disclosure which is incorporated herein by reference), analogs and the like.

As used herein, the term "about" as a modifier to a quantity is intended to mean + or −10% inclusive of the quantity being modified.

As used herein, the term "aliphatic" refers to a non aromatic hydrocarbon in which the carbon atoms are either straight or branch chain or cyclic and either saturated or unsaturated.

The term "effective amount" or "a therapeutically effective amount" of a drug or pharmacologically active agent is intended to mean a nontoxic but sufficient amount of the drug or active agent for providing the desired therapeutic effect. The amount that is "therapeutically effective" will vary from subject to subject, depending on the age and general condition of the individual, the particular active agent or agents, and the like. An appropriate "therapeutically effective" amount in any individual case may be determined by one of ordinary skill in the art using routine experimentation.

The term "transdermal patch" is intended to refer to a self-contained, discrete dosage form that, when applied to skin, is designed to deliver the drug(s) through the skin into systemic circulation. Some important characteristics of a transdermal patch include flux rate, lag time and stability. Flux rate relates to the rate at which the transdermal patch delivers pramipexole. Lag time relates to the time required for pramipexole blood concentration to reach steady state after application of the transdermal patch. Lag time preferably matches pramipexole metabolization rate in order to minimize fluctuations in blood concentration between applications of successive transdermal patches. Lastly, stability relates to the amount of impurities that develops within the transdermal patch while in storage.

Flux rate and lag time differ substantially for a daily transdermal patch as compared to a week-long pramipexole transdermal patch. The reason is that administration of daily transdermal patch by definition requires interruption of drug delivery once a day, so when a replacement daily transdermal patch is applied, the new patch needs to provide higher flux rate and shorter lag time to quickly ramp up delivery of pramipexole to the patient in order to maintain constant pramipexole blood concentration while minimizing blood concentration fluctuation. Specifically, the daily pramipexole transdermal patch preferably provides a steady state flux rate at about 0.8 $\mu g/cm^2$ hr and up to about 13 $\mu g/cm^2$ hr as well as a lag time of less than about 8 hours.

Further differences between the daily and weekly pramipexole transdermal patch is that the daily transdermal patch of the present invention is able to tolerate moisture in contrast with week-long pramipexole transdermal patches. Tolerance for moisture is possible for the daily transdermal patch of the present invention because it contains lower drug loading and has substantially shorter therapeutic duration than week-long patches. In addition, the lower drug loading also allows smaller patch size than the week-long patches. For example, in one embodiment, the daily pramipexole transdermal patch of the present invention may be about 30 $cm^2$ or less. The tolerance for moisture and smaller patch size both help to reduce risks for and severity of skin irritation.

The pramipexole transdermal patch of the present invention comprises a drug-containing layer that comprises pramipexole free base or a pharmaceutically acceptable salt thereof as the active pharmaceutical ingredient. The pramipexole or the pharmaceutically acceptable salt thereof may comprise pramipexole free base, pramipexole dihydrochloride or dexpramipexole The pramipexole drug-containing layer of the transdermal patch of the present invention further comprises one or more polymers for housing pramipexole that play a significant role in determining pramipexole flux rate. Specifically, higher flux rate may be achieved by lowering the solubility of the pramipexole within the polymer(s) relative to the solubility within the stratum corneum layer of the user's skin.[6] However, low solubility of pramipexole can cause crystallization of pramipexole within the skin patch, reducing the amount of pramipexole available to be delivered to a user.

[6] J. W. Wiechers, C. I., Kelly, T. G. Blease and J. C. Dederen, Formulating for Efficacy, *International Journal of Cosmetic Science*, 2004, 26, 173-183

In addition, low solubility of respective ingredients of the transdermal patch, or low miscibility, could present manufacturing issues as it could prevent even distribution of pramipexole within the polymers and cause phase separation.

Therefore, solubility of pramipexole within the polymers and miscibility of respective components of the transdermal patch are important considerations that necessitate proper balancing when selecting polymers and creating formulations using the selected polymers for the transdermal patch of the present invention.

One possible class of polymers for use in the pramipexole transdermal patch of the present invention is acrylate-based polymers. Acrylate-based polymers are used extensively in transdermal drug delivery systems since they are relatively low in cost compared to other polymers, provides high solubility for a variety of drugs including pramipexole and pharmaceutically acceptable salt thereof, adhere well to a variety of different surfaces and capable of being formulated to provide adhesive property.

Acrylate polymers may comprise copolymers of various monomers which may be "soft" monomers or "hard" monomers or combinations thereof. Soft monomers are characterized by having lower glass transition temperature. Examples of soft monomers include, but not limited to, n-butyl acrylate, 2-ethylhexyl acrylate and isooctyl acrylate. Hard monomers are characterized by having higher glass transition temperature. Examples of hard monomers include, but not limited to methyl methacrylate, ethyl acrylate and methyl acrylate. Soft monomers with lower glass transition temperature generally have higher solubility and better stability compared to hard monomers.

Monomers from which the acrylate polymers may be produced may comprise acrylic acid, methacrylic acid, butyl acrylate, butyl methacrylate, hexyl acrylate, hexyl methacrylate, isooctyl acrylate, isooctyl methacrylate, glycidyl methacrylate, 2-hydroxyethyl acrylate, methyl acrylate, methylmethacrylate, 2-ethylhexyl acrylate and 2-ethylhexyl methacrylate. Additional examples of acrylic adhesive monomers are described in Satas, "Acrylic Adhesives," Handbook of Pressure-Sensitive Adhesive Technology, 2nd ed., pp. 396-456 (D. Satas, ed.), Van Nostrand Reinhold, New York (1989).

Acrylate polymers may comprise bipolymer, terpolymer or tetrapolymer or copolymers of even greater numbers of monomers, including copolymers of alkyl acrylates, alkyl methacrylates, copolymerizable secondary monomers and/or monomers having functional groups.

In addition, the acrylic-based polymers may have hydroxyl functional group and/or carboxyl functional groups which can influence properties of the polymers such as solubility of pramipexole, miscibility with other components of the transdermal patch as well as pramipexole flux rate. The influence of functional groups is polymer dependent, and therefore, difficult to predict.

Moreover, the acrylic-based polymers may also contain cross-linkers that provide chemical bonds between polymer chains so as to mitigate cold flow within the transdermal patch of the present invention. In some embodiments, the cross-linkers comprise about 0.01% to about 6% by weight of the drug-containing layer. Examples of cross-linkers that may be used with acrylic-based polymers containing hydroxyl functional group include but are not limited to polybutyl titanate (PBT), tetrabutyl titanate (TBT), titanium dialkoxide bis(acetylacetonate) and/or titanium metal chelate. Examples of cross-linkers that may be used with acrylic-based polymers containing carboxyl functional group include but are not limited to aluminum tris(acetyl acetonate) and/or aluminium metal chelate. In addition, the acrylic-based polymers may be combined with tackifiers to provide adhesive property.

Examples of commercially available acrylic-based polymer that are acrylic-hydrocarbon hybrid polymers may be sourced from polymer solutions including, but not limited to, Duro-Tak™ 87-502B and Duro-Tak™ 87-504B, Duro-Tak™ 87-502A, Duro-Tak™ 87-503A and Duro-Tak™ 87-504A. Examples of acrylate-based polymers with no functional group may be sourced from polymer solutions including, but not limited to, Duro-Tak™ 87-4098, Duro-Tak™ 87-900A and Duro-Tak™ 87-9301. Examples of acrylate-based polymers having carboxyl functional group may be sourced from solutions including, but not limited to, Duro-Tak™ 87-235A, Duro-Tak™ 87-2353, Duro-Tak™ 87-2852, Duro-Tak™ 87-2051, Duro-Tak™ 87-2052, Duro-Tak™ 87-2054, Duro-Tak™ 87-2194 and Duro-Tak™ 87-2196. Examples of acrylate-based polymers having hydroxyl functional group may be sourced from solutions including, but not limited to Duro-Tak™ 87-2510, Duro-Tak™ 87-2287, Duro-Tak™ 87-4287 and Duro-Tak™ 87-2516. Examples of acrylate-based polymers having both hydroxyl and carboxyl functional groups may be sourced from solution including, but not limited to Duro-Tak™ 87-2074 and Duro-Tak™ 87-2979.

TABLE 1

Typical Physical Properties

| Product | Description | Contains vinyl acetate | Contains Crosslinker | Solids (%) | Viscosity (cP or mPa-s) |
|---|---|---|---|---|---|
| Duro-Tak 87-900A | acrylates copolymer | No | n/a | 43 | 1800 |
| Duro-Tak 87-9301 | acrylates copolymer | No | n/a | 36.5 | 9500 |
| Duro-Tak 87-4098 | acrylates copolymer | Yes | n/a | 38.5 | 6500 |
| Duro-Tak 87-2510 | acrylates copolymer | No | No | 40.5 | 4250 |
| Duro-Tak 87-2287 | acrylates copolymer | Yes | No | 50.5 | 18000 |
| Duro-Tak 87-4287 | acrylates copolymer | Yes | No | 39 | 8000 |
| Duro-Tak 87-2516 | acrylates copolymer | Yes | Yes | 41.5 | 4350 |
| Duro-Tak 87-2074 | acrylates copolymer | No | Yes | 29.5 | 1500 |
| Duro-Tak 87-235A | acrylates copolymer | No | No | 36.5 | 8000 |
| Duro-Tak 87-2353 | acrylates copolymer | No | No | 36.5 | 8000 |
| Duro-Tak 87-2852 | acrylates copolymer | No | Yes | 33.5 | 2500 |
| Duro-Tak 87-2051 | acrylates copolymer | Yes | No | 51.5 | 4000 |
| Duro-Tak 87-2052 | acrylates copolymer | Yes | Yes | 47.5 | 2750 |
| Duro-Tak 87-2054 | acrylates copolymer | Yes | Yes | 47.5 | 2750 |
| Duro-Tak 87-2194 | acrylates copolymer | Yes | Yes | 45 | 3000 |
| Duro-Tak 87-2196 | acrylates copolymer | Yes | Yes | 45 | 2100 |
| Duro-Tak 87-2979 | acrylates copolymer | Yes | — | 44.5 | 2700 |
| Duro-Tak 87-2825 | acrylates copolymer | Yes | — | 47.5 | 1650 |
| Duro-Tak 87-2525 | acrylates copolymer | Yes | — | 41.5 | 4350 |

TABLE 2

| Adhesive | Description | Functional group | API solubility |
|---|---|---|---|
| DURO-TAK 87-2979 | acrylate-vinylacetate | —COOOH/—OH | 10% |
| DURO-TAK 87-2054 | acrylate-vinylacetate | —COOH | 10% |
| DURO-TAK 87-2510 | Acrylic | —OH | 5% |
| DURO-TAK 87-4287 | acrylate-vinylacetate | —OH | 8% |

In order to take advantage of desired properties such as high flux while minimizing undesirable properties such as low solubility or tendency to cause crystallization, rather than using only a single polymer, polymers with different characteristics may be combined to realize superior properties. Therefore, in some embodiments, the pramipexole transdermal patch of the present invention may comprise a combination of two or more polymers. In one embodiment, the two polymers may comprise two acrylate-based polymers. In addition, each polymer may comprise a carboxyl functional group, a hydroxyl functional group or both functional groups.

However, when considering combining multiple polymers in a transdermal patch, adequate miscibility between the polymers becomes important to avoid issues such as layering and phase separation. Experiments were performed Experiments were performed to evaluate the solubility of pramipexole in various polymers with results listed in Table 2 with experiment detailed in Example 1 below. We found that solubility of below 5% would prevent proper distribution of pramipexole within the transdermal patch. Among the polymers tested, the carboxyl and hydroxyl groups-containing acrylic polymer sourced from Duro-Tak 87-2979, the carboxyl group-containing acrylic polymer sourced from Duro-Tak 87-2054 and the hydroxyl group-containing acrylic polymer sourced from Duro-Tak 87-2510 and Duro-Tak 87-4287 provided adequate solubility.

to evaluate the miscibility of various combinations of acrylate-based pressure sensitive adhesives. Some of the results are summarized in Table 3.

TABLE 3

| Polymer 1 90% (w/w) | Polymer 2 10% (w/w) | Observation |
|---|---|---|
| DURO-TAK 87-2054 (carboxyl functional group) | DURO-TAK 87-2510 (hydroxyl functional group) | Miscible |
| DURO-TAK 87-2054 (carboxyl functional group) | DURO-TAK 87-4287 (hydroxyl functional group) | Miscible |

Lag time is another important consideration for the daily pramipexole transdermal patch of the present invention and can be influenced by permeation enhancers.

Suitable enhancer compositions may include, but is not limited to, aliphatic alcohols, such as but not limited to saturated or unsaturated higher alcohols having 12 to 22 carbon atoms, such as oleyl alcohol and lauryl alcohol; saturated or unsaturated fatty acid having a chain of 8 to 20 carbons, such as but not limited to linolic acid, oleic acid, linolenic acid, stearic acid, isostearic acid and palmitic acid; fatty acid esters, such as but not limited to isopropyl myristate, diisopropyl adipate and isopropyl palmitate; alcohol amines, such as but not limited to triethanolamine, triethanolamine hydrochloride and diisopropanolamine; polyhydric alcohol alkyl ethers, such as but not limited to alkyl ethers of polyhydric alcohols such as glycerol, ethylene glycol, propylene glycol, 1,3-butylene glycol, diglycerol, polyglycerol, diethylene glycol, polyethylene glycol, dipropylene glycol, polypropylene glycol, sorbitan, sorbitol, isosorbide, methyl glucoside, oligosaccharides and reducing oligosaccharides, where the number of carbon atoms of the alkyl group moiety in the polyhydric alcohol alkyl ethers is preferably 6 to 20; polyoxyethylene alkyl ethers, such as but not limited to polyoxyethylene alkyl ethers in which the number of carbon atoms of the alkyl group moiety is 6 to 20, and the number of repeating units (e.g. —OCH2CH2-) of the polyoxyethylene chain is 1 to 9, such as but not limited to diethylene glycol monoethyl ether, polyoxyethylene lauryl ether, polyoxyethylene cetyl ether, polyoxyethylene stearyl ether and polyoxyethylene oleyl ether; glycerides (i.e., fatty acid esters of glycerol), such as but not limited to glycerol esters of fatty acids having 6 to 18 carbon atoms, where the glycerides may be monoglycerides (i.e., a glycerol molecule covalently bonded to one fatty acid chain through an ester linkage), diglycerides (i.e., a glycerol molecule covalently bonded to two fatty acid chains through ester linkages), triglycerides (i.e., a glycerol molecule covalently bonded to three fatty acid chains through ester linkages), or combinations thereof, where the fatty acid components forming the glycerides include, but are not limited to octanoic acid, decanoic acid, dodecanoic acid, tetradecanoic acid, hexadecanoic acid, octadecanoic acid (i.e., stearic acid) and oleic acid; middle-chain fatty acid esters of polyhydric alcohols with aliphatic tails of 6-20 carbon atoms; alkyl esters such as but not limited to lactic acid alkyl esters and dibasic acid alkyl esters with chain of 1 to 6 carbon atoms; acylated amino acids; pyrrolidone; pyrrolidone derivatives; and combinations thereof.

In certain embodiments, suitable enhancer compositions include, but are not limited to ethoxylated fatty alcohols, such as but not limited to polyethylene glycol ethers, polyoxyethers of lauryl alcohol, polyethylene glycol ether of cetyl alcohol, polyethylene glycol ethers of stearic acid, polyethylene glycol ethers of oleyl alcohol, polyoxyethylene ethers of a mixture of cetyl alcohol and stearyl alcohol, ethoxylated linear alcohol, and combinations thereof.

In certain embodiments, suitable enhancer compositions include, but are not limited to lactic acid, tartaric acid, 1,2,6-hexanetriol, benzyl alcohol, lanoline, potassium hydroxide (KOH), and tris(hydroxymethyl)aminomethane. Other suitable permeation enhancers may comprise glycerol monooleate (GMO) and sorbitan monolaurate (SML), lactate esters such as lauryl lactate, methyl lactate, caproyl lactic acid, lauramide diethanolamine (LDEA), dimethyl lauramide, polyethylene glycol-4 lauryl ether (Laureth-4), lauryl pyroglutamate (LP), sorbitan monolaurate, ethanol and combinations thereof.

Permeation enhancers may also comprise surfactants including combinations of semi-polar solvents, e.g., propylene glycol, butane diol, N-methylpyrrolidone, dimethyl sulfoxide, diethylene glycol methyl ether and dimethyl isosorbide. Other surfactant permeation enhancers may comprise isopropyl myristate, oleic acid, lauryl lactate and combinations thereof.

Furthermore, in certain embodiments, permeation enhancer may comprise squalane, isopropyl palmitate, isopropyl myristate, sorbitan laurate, DL-limonene, ethyl oleate, methyl dodecanoate, propylene glycol dicaprylocaprate, propylene glycol dicaprylate/dicaprate, Labrafac™ PG, octyl alcohol, dodecyl alcohol, polyoxyethylene (4) lauryl ether, Brij® 30, oleyl alcohol, polyoxyethylene sorbitan monooleate, Tween®80, propylene glycol, diethylene glycol, monoethyl ether, propylene glycol monocaprylate, Capryol PGMC, 1-methyl-2-pyrrolidinone, glyceryl triacetate, triacetin, polyoxyl castor oil, Kolliphor® RH40, oleoyl macrogol-6 glycerides, Labrafil™ M1944CS, linoleoyl polyoxyl-6 glycerides, Labrafil™ M2125CS, caprylocaproyl macrogol-8 glycerides, Labrasol®, polyoxyl castor oil, oleoyl macrogol-6 glycerides, linoleoyl polyoxyl-6 glycerides, caprylocaproyl macrogol-8 glycerides and N-methyl pyrrolidone.

Numerous permeation enhancers were evaluated to identify suitable permeation enhancers, including permeation enhancers listed in Table 4 below that lists solubility of pramipexole in the respective permeation enhancers. Preferred permeation enhancers that provide good solubility include fatty acid such as oleic acid, saturated or unsaturated fatty alcohol having 8-26 carbon atoms such as octanol and oleyl alcohol, surfactants such as Tween 80 and Brij 30, and solvents such as Transcutal P, isopropyl alcohol, methanol, propylene glycol (PG) and ethyl acetate.

TABLE 4

| Enhancer | Category | Solubility of Pramipexole (mg/mL) |
|---|---|---|
| Oleic Acid | Fatty acid | 58.96 |
| Methyl Laurate | Fatty acid ester | 7.07 |
| Octanol | Fatty alcohol | 113.04 |
| Oley Alcohol | Fatty alcohol | 113.04 |
| Limonene | Solvent | 5.34 |
| Ethyl Acetate | Solvent | 34.28 |
| Propylene Glycol (PG) | Solvent | 55.61 |
| Methanol | Solvent | 100.08 |
| Isopropyl Alcohol | Solvent | 106.67 |
| Transcutal P | Solvent | 121.99 |
| Tween 80 | Surfactants | 86.07 |
| Brij 30 | Surfactants | 111.14 |

Figure 2:
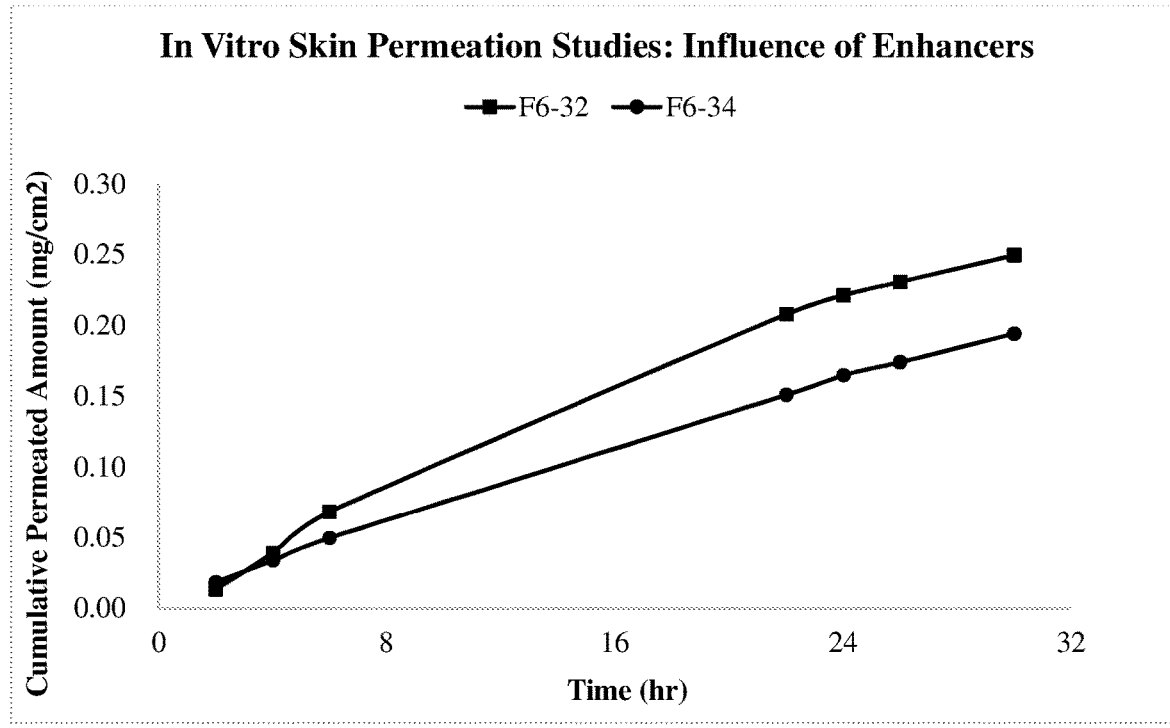
FIG. 2 illustrate in vitro influence of permeation enhancers on pramipexole permeation. The figure shows cumulative permeated pramipexole amount in mg/cm² versus time in hours for about 30 hours for formulations F6-32 and F6-34, wherein the two formulations differ only in the selection of the permeation enhancers. For example, F6-32 comprises a combination of methyl laurate and propylene glycol permeation enhancers whereas F6-34 comprises a combination of methyl laurate and Brij 30 permeation enhancers.

Moreover, Example 2 and FIG. 2 detail some of our experimentation with various permeation enhancers using formulations F6-32 and F6-34 that differ only in one permeation enhancer, namely F6-32 uses propylene glycol whereas F6-34 uses Brij 30. As shown in FIG. 2, the difference in only one permeation enhancer resulted in more than 30% difference in cumulative permeated amount of pramipexole. Therefore, permeation enhancers can substantially influence the flux rate and lag time of the daily transdermal patch of the present invention.

However, one major issue with permeation enhancers is that they can cause skin irritation. To minimize this problem, content of each permeation enhancer may be reduced without compromising permeation enhancing effects by combining two or more permeation enhancers. Therefore, in some embodiments, the pramipexole transdermal patch of the present invention comprises a combination of two or more permeation enhancers. In other embodiments, the pramipexole transdermal patch of the present invention comprises a combination of aliphatic alcohols, fatty acids, fatty acid esters, alcohol amines, polyhydric alcohol alkyl ethers, polyoxyethylene alkyl ethers, glycerides, middle-chain fatty acid esters of polyhydric alcohols, lactic acid alkyl esters, dibasic acid alkyl esters, acylated amino acids, pyrrolidone, pyrrolidone derivatives, ethoxylated fatty alcohols and/or surfactants. In another embodiment, the pramipexole transdermal patch of the present invention comprises a combination of fatty acids and/or fatty alcohols, such as oleic acid and lauric acid, oleic acid and lauryl alcohol, oleyl alcohol and lauric acid or oleyl alcohol, lauryl alcohol, surfactants or a combination thereof.

Importantly, in our experimentations with various combinations of permeation enhancers, we surprisingly found that combinations of permeation enhancers that provide higher flux also has higher pramipexole solubility. This finding is contrary to conventional understanding that higher flux is typically associated with lower solubility as discussed earlier in connection the Wiechers et al. reference. Specifically, combinations of permeation enhancers with pramipexole solubility greater than about 50 mg/mL provided higher flux rate than those combinations with lower solubility. Therefore, in an embodiment, the daily pramipexole transdermal patch of the present invention comprises a combination of permeation enhancers with pramipexole solubility equal or higher than about 50 mg/mL.

Given the various properties of the polymers and permeation enhancer, numerous formulations were created using various combinations of polymers and permeation enhancers as listed in Table 5. As illustrated in the flux results summarized in Table 5, we found that certain combinations result in potentiation that provide surprisingly high flux rate.

TABLE 5

| Formulation | F6-20 | F6-24 | F6-31 | F6-32 | F6-33 | F6-34 | F6-35 | F6-36 |
|---|---|---|---|---|---|---|---|---|
| DT504B | | | | | | | | |
| DT502B | | | | | | | | |
| DT2054 (-COOH) | 37.5 | 40 | 38.5 | 27 | 29 | 27 | 41 | 41 |
| DT2852 (-COOH) | | | | | | | | |
| DT2510 (-OH) | 37.5 | 40 | | | | | 41 | 41 |
| DT4287 (-OH) | | | 38.5 | 50 | 53 | 50 | | |
| Pramipexole Base | 10 | 10 | 8 | 8 | 8 | 8 | 8 | 8 |
| Methyl laurate | 10 | | 10 | 10 | | 10 | | |
| Propylene glycol | 5 | | | 5 | 5 | | | |
| Transcutol P | | 5 | | | 5 | | | |
| Brij 30 | | 5 | 5 | | 5 | 5 | | |
| Ethyl Oleate | | | | | | | 5 | |
| Oleic acid | | | | | | | 5 | |
| Isopropyl Myristate | | | | | | | | 5 |
| Lauryl Alcohol | | | | | | | | 5 |
| Flux rate (µg/cm²-hr) | 9.3 | 10 | 6.9 | 8.6 | 7.5 | 6.3 | 2.3 | 4.7 |

Figure 3:
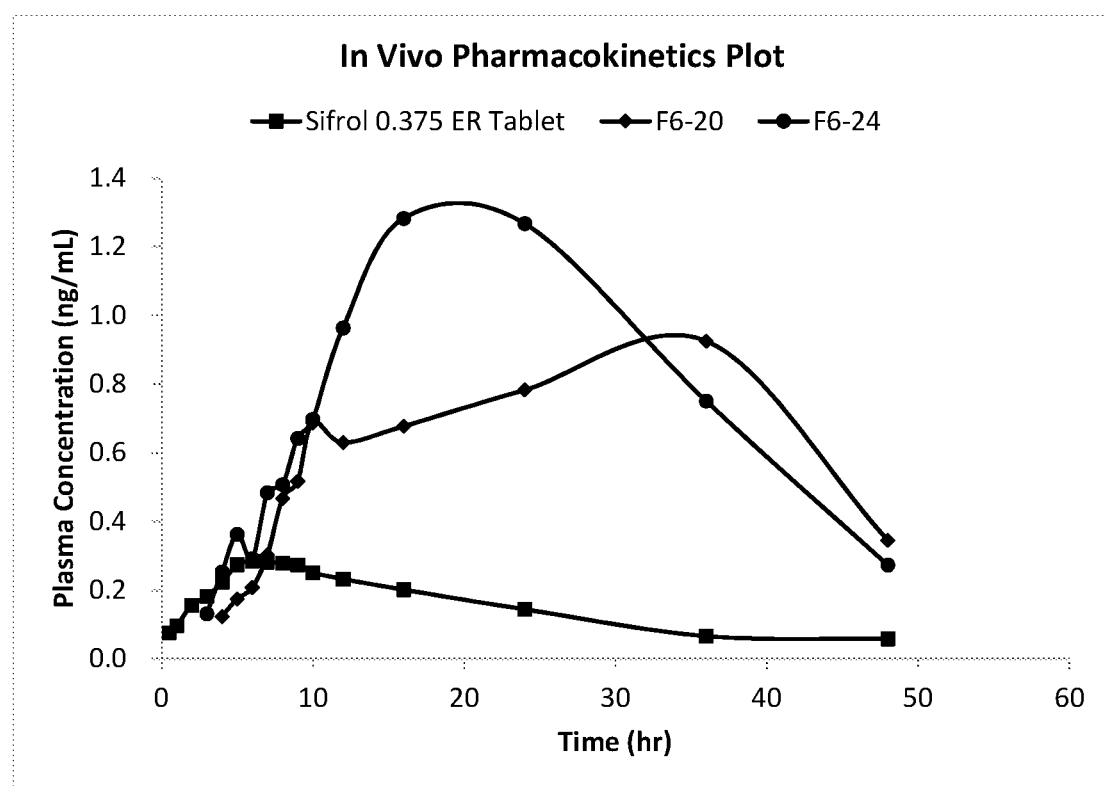
FIG. 3 illustrate pramipexole plasma concentration profile in ng/mL versus time in hours over the first 48 h after administration of formulations F6-20 and F6-24 as well as the reference Sifrol® 0.375 ER tablet.

As Table 5 illustrates, formulations F6-20, F6-24, F6-31, F6-32, F6-33, F6-34, F6-35 and F6-36 each exhibit steady state pramipexole flux rate in a range of about 2.3 to about 10 µg/cm²-hr, all above the desired minimum flux rate of about 0.8 µg/cm²-hr. Surprisingly, each of the formulations comprises a carboxyl group-containing acrylic polymer in combination with a hydroxyl group-containing acrylic polymer. These high flux rates are in stark contrast to substantially lower flux rate for formulations that we tested that do not comprise a carboxyl group-containing acrylic polymer in combination with a hydroxyl group-containing acrylic polymer. In many cases, the difference in flux rates are more than an order of magnitude lower. This indicates that a carboxyl group-containing acrylic polymer in combination with a hydroxyl group-containing acrylic polymer result in potentiation. For example, Duro-Tak™ 87-2054 containing acrylic polymer with carboxyl functional group, in combination with an acrylic polymer with hydroxyl functional group results in potentiation with respect to achieving high flux rate. In addition, these formulations avoided crystallization and miscibility issues while providing desired flux rate, demonstrating proper selection and proportion of various components. In addition, Example 3 and FIG. 3 illustrate that the two formulations with the highest flux rate F-20 and F-24 each have lag time of about 3 to 4 hour, after which they are able to maintain up to about 30 hours of steady pramipexole blood concentration. It is notable that the Reference Sifrol® tablets provided a substantially greater fluctuation in blood concentration. Furthermore, as shown in Table 6, both formulations F-20 and F-24 have good stability characteristics. Specifically, after storage at 60° C. at 75% relative humidity for 14 days, both formulations contain substantially less than 1% WW impurities.

TABLE 6

| Formulation # | Stress Condition | Test Interval | Assay % w/w | Impurities (% W/W) | | | | | Total impurities |
|---|---|---|---|---|---|---|---|---|---|
| | | | | RRT 0.3 | RRT 0.41 | RRT 0.43 | RRT 0.52 | ACBR[1] RRT 0.62 | |
| F6-20 | 60° C./75% RH | Initial | 106.5 | 0.04 | — | 0.05 | — | 0.1 | 0.19 |
| | | 7 Days | 110.54 | 0.05 | 0.09 | 0.09 | — | 0.15 | 0.37 |
| | | 14 Days | 110.51 | — | 0.11 | 0.07 | — | 0.15 | 0.33 |
| F6-24 | 60° C./75% RH | Initial | 95.4 | — | 0.1 | 0.09 | — | 0.13 | 0.33 |
| | | 7 Days | 95.46 | — | 0.06 | 0.06 | — | 0.11 | 0.23 |
| | | 14 Days | 94.23 | 0.03 | — | 0.03 | — | 0.06 | 0.13 |

Therefore, in an embodiment, the pramipexole transdermal patch of the present invention comprises a carboxyl group-containing acrylic polymer in combination with hydroxyl group-containing acrylic polymer. More specifically, the pramipexole transdermal patch of the present invention comprises polymers sourced from Duro-Tak™ 87-2054 in combination with polymers sourced from Duro-Tak™ 87-2510 or Duro-Tak™ 87-4287.

In some embodiments, the weight ratio of the content of the carboxyl group-containing acrylic adhesive to the content of the hydroxyl group-containing acrylic adhesive is from about 5:1 to about 1:5; preferably from about 4:1 to about 1:4; more preferably from about 3:1 to about 1:3; and even more preferably from about 2:1 to about 1:2.

In other embodiments, the pramipexole is in a free base form. The amount of pramipexole in the matrix is from about 2 to about 10%; preferably from about 4 to about 10%; more preferably from about 6 to about 10%; and even more from about 8 to about 10%.

In some embodiments, the permeation enhancers, comprise aliphatic alcohols, fatty acids, fatty acid esters, alcohol amines, polyhydric alcohol alkyl ethers, polyoxyethylene alkyl ethers, glycerides, ethoxylated fatty alcohols, or a combination thereof. In other embodiments, the permeation enhancers comprise methyl laurate, propylene glycol, transcutol P, brij 30, ethyl oleate, oleic acid, isopropyl myristate, lauryl alcohol, surfactants or a combination thereof.

The total amount of the permeation enhancers in the matrix may comprise from about 10 to about 15%. In some embodiments, the pramipexole transdermal patch of the present invention comprises two permeation enhancers in a total amount of 10% of the matrix. In some embodiments, the pramipexole transdermal patch of the present invention comprises two permeation enhancers in a total amount of about 15% of the matrix. In some embodiments, the pramipexole transdermal patch of the present invention comprises three permeation enhancers in a total amount of 15% of the matrix.

In some embodiments, the pramipexole transdermal patch of the present invention comprises a combination of methyl laurate and propylene glycol permeation enhancers wherein the weight ratio of the content of methyl laurate to the content of propylene glycol is about 2:1.

In some embodiments, the pramipexole transdermal patch of the present invention comprises a combination of Transcutol P and Brij 30 wherein the weight ratio of the content of Transcutol P to the content of Brij 30 is preferably about 1:1.

In some embodiments, the pramipexole transdermal patch of the present invention comprises a combination of ethyl oleate and oleic acid wherein weight ratio of the content of ethyl oleate to the content of oleic acid is preferably about 1:1.

In some embodiments, the pramipexole transdermal patch of the present invention comprises a combination of isopropyl myristate and lauryl alcohol wherein the weight ratio of the content of isopropyl myristate to the content of lauryl alcohol is preferably about 1:1.

In some embodiments, the pramipexole transdermal patch of the present invention comprises a combination of propylene glycol, Transcutol P and Brij 30 wherein the weight ratio of the content of propylene glycol to the content of Transcutol P to the content of Brij 30 is preferably about 1:1:1.

II. Preparation of Pramipexole Transdermal Patch

The pramipexole transdermal patch may be formulated in accordance with procedures disclosed in the prior art such as CN 103432,104; US publication 2016/0113908 and Tingting et al. AAPS Pharma SciTech (2016) published online May 31, 2016, the disclosures of which are incorporated herein by reference.

For example, the daily pramipexole transdermal patch of the present invention may be made by preparing a blend of an appropriate amount of one or more polymer solutions such as Duro-Tak™ 87-2054, Duro-Tak™ 87-2510 or Duro-Tak™ 87-4287. These polymer solutions may comprise solvents such as ethyl acetate, heptane, n-heptane, hexane methanol, ethanol, isopropanol, 2,4-pentanedione, toluene, xylene or a combination thereof. Next, pramipexole or a pharmaceutically acceptable salt thereof, permeation enhancers as well as tackifier are added to the blend. Importantly, the blend should have viscosity of between about 0.1 to 18 Pascal seconds (Pa·s), as low viscosity prevents formation of the drug-containing layer and high viscosity can create a drug containing layer of uneven thickness with uneven distribution of the drug.

The blend is then cast onto a release liner for drying at appropriate drying conditions to form the drug-containing layer. During the drying process, the solvent(s) are evaporated so that only a trace remains. After the drying process, the drug-containing layer is then laminated on one side onto a backing film while a release liner is applied onto the other side of the drug-containing layer.

III. Uses of Pramipexole Transdermal Patch

On application to the skin, the pramipexole in the matrix of the patch diffuses into the skin where it is absorbed into the bloodstream to produce a systemic drug effect. The onset of the drug effect depends on various factors, such as, potency of the pramipexole, the solubility and diffusivity of the pramipexole in the skin, thickness of the skin, concentration of the pramipexole within the skin application site, concentration of the pramipexole in the matrix, and the like. The daily pramipexole transdermal patch of the present invention is kept on the skin for 24 hours without removal until the end of the 24-hour period at which point a new daily pramipexole transdermal patch of the present invention is applied soon after to minimize fluctuations in pramipexole blood concentration.

The representative examples which follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that, unless otherwise indicated, the entire contents of each of the references cited herein are incorporated herein by reference to help illustrate the state of the art. The following examples contain important additional information, exemplification and guidance which can be adapted to the practice of this invention in its various embodiments and the equivalents thereof.

These and other aspects of the present invention will be further appreciated upon consideration of the following Examples, which are intended to illustrate certain particular embodiments of the invention but are not intended to limit its scope, as defined by the claims.

EXAMPLES

Example 1: In Vitro Skin Permeation Studies—Effect of Pressure-Sensitive Adhesives Flux rate of the pramipexole transdermal patch of the present invention is measured with a standard procedure using Franz diffusion cells and human cadaver skin as described in Strasinger C., Raney S., Tran D., Ghosh P., Newman B, Bashaw E., Ghosh T. and Shukla C., Navigating sticky areas in transdermal product development, Journal of Controlled Release: 233 (2016) 1-9.

Specifically, in each Franz diffusion cell a disc (diameter of 25 mm) of human cadaver skin is placed on the receptor compartment. A transdermal delivery system is cut the same size as the skin and placed over the diffusion area in the center of the receptor. The donor compartment is then added and clamped to the assembly. At time 0, receptor medium solution 14 mL is added into the receptor compartment and the cell maintained at 32° C. Samples of the receptor compartment are taken periodically to determine the skin flux and analyzed by HPLC. The pramipexole concentration in the sampled solution was assayed by HPLC, and the flux value (value of the skin permeation rate of the drug in a steady state) and 24-hour cumulative permeation were calculated.

Various formulations were prepared according to the transdermal patch preparation procedures described above. FIG. 1 plots the cumulative permeated amount for transdermal patch made from Duro Tak 87-2852, Duro Tak 87-2510, Duro Tak 87-2054 and Duro Tak 87-4287. As FIG. 1 illustrates, various polymers result in vastly different cumulative permeation. It is notable that polymers with hydroxyl functional group tends to provide higher flux rate compared to polymers with carboxyl functional group.

Example 2: In Vitro Skin Permeation Studies—Effect of Permeation Enhancers

Cumulative permeated amount for formulations F6-32 and F6-34 is obtained using the same method as described in Example 1 with results shown in Table 4. Both formulations comprise the same components except for the permeation enhancer. Specifically, both formulations comprise pramipexole free base 8% (w/w), DT2054 27% (w/w) and DT4287 50% (w/w). However, formulation F6-32 comprises methyl laurate 10% (w/w) and propylene glycol 5% (w/w) as permeation enhancers whereas formulation F6-34 comprises methyl laurate 10% (w/w) and Brij 30 5% (w/w) as permeation enhancers. Cumulated permeated amount of pramipexole in the in-vitro skin permeation study during 24 hours was 0.221 mg/cm$^2$ for F6-32, and 0.165 mg/cm$^2$ for F6-34, a difference of over 30% that demonstrate the significant influence of permeation enhancers on flux rate and lag time.

Example 3: Pharmacokinetics of Pramipexole Transdermal Patch

The pharmacokinetics studies of formulations F6-20 and F6-24 were assessed in 12 healthy volunteers. The transdermal system is applied to healthy subjects topically on their upper chest for a day. The blood samples were collected periodically.

The mean pramipexole plasma concentration in ng/mL versus time in hours of two test formulations F6-20 and F6-24 as well as the reference, Sifrol 0.375 ER tablet, are shown in FIG. 3. As FIG. 3 illustrates, formulations F6-20 and F6-24 both have lag time of about 4 and about 3 hours respectively, which are within the desired about 8 hours or less. In addition, F6-20 and F6-24 are able to provide substantially stable plasma concentration at about 0.2 ng/mL and 0.8 ng/mL, respectively, for more than 20 hours after the initial lag time. In contrast, the results show that Sifrol tablet provides large fluctuation in plasma concentration tracing out a parabola over the same period on the same figure.

Although the present invention has been described in terms of specific exemplary embodiments and examples, it can be appreciated by those skilled in the art that changes could be made to the examples described above without departing from the broad inventive concept thereof. It is understood, therefore, that this invention is not limited to the particular examples disclosed, but it is intended to cover modifications within the spirit and scope of the present invention as defined by the appended claims.

It is to be understood that both the foregoing general description and the following detailed description are exemplary and explanatory only and are not restrictive of the invention, as claimed.

These and other changes can be made to the technology in light of the detailed description. In general, the terms used in the following disclosure should not be construed to limit the technology to the specific embodiments disclosed in the specification, unless the above detailed description explicitly defines such terms. Accordingly, the actual scope of the technology encompasses the disclosed embodiments and all equivalent ways of practicing or implementing the technology.

What is claimed is:

1. A transdermal patch for administration comprising:
   (i) a drug-containing layer;
   (ii) a backing layer; and
   (iii) a protective layer,
wherein the drug-containing layer comprises:
   (a) pramipexole or a pharmaceutically acceptable salt thereof,
   (b) a combination of at least two permeation enhancers, wherein the permeation enhancers are selected from the group consisting of aliphatic alcohols, fatty acids having a chain of 8 to 20 carbons, fatty acid esters, alcohol amines, polyhydric alcohol alkyl ethers, polyoxyethylene alkyl ethers, glycerides, middle-chain fatty acid esters of polyhydric alcohols having a chain of 8-20 carbon atoms, alkyl esters having a chain of 1-6 carbon atoms, acylated amino acids, pyrrolidone, pyrrolidone derivatives, ethoxylated fatty alcohols, pharmaceutically acceptable surfactants and combinations thereof,
   (c) a carboxyl functional group containing acrylic-based polymer comprising an acrylate copolymer of 2-ethylhexyl acrylate, vinyl acetate, butyl acrylate, acrylic acid and a crosslinker consisting of aluminum tris(acetyl acetonate) or an aluminium metal chelate, and
   (d) a hydroxyl functional group containing acrylic-based polymer comprising an acrylate copolymer of 2-ethylhexyl acrylate, methyl acrylate and 2-hydroxyethyl acrylate or an acrylate copolymer of 2-ethylhexyl acrylate, vinyl acetate and 2-hydroxyethylacrylate;
wherein the carboxyl group-containing acrylic-based polymer and the hydroxyl group-containing acrylic-based polymer are in a ratio of from about 2:1 to about 1:2 by weight, wherein the transdermal patch provides flux rate of between about 6.3 μg/cm$^2$ hr and about 10 μg/cm$^2$ hr for up to about 40 hours, wherein lag time for the transdermal patch is about 8 hours or less, and wherein at least one permeation enhancer has pramipexole solubility of between about 50 mg/mL to about 122 mg/mL.

2. The transdermal patch of claim 1, wherein the pramipexole or its pharmaceutically acceptable salt thereof is selected from pramipexole free-base, pramipexole dihydrochloride or dexpramipexole.

3. The transdermal patch of claim 1, wherein the pramipexole or its pharmaceutically acceptable salt thereof is in an amount from about 2% to about 15% by weight of the drug-containing layer.

4. The transdermal patch of claim 1, wherein an impurity level within pramipexole is about 1.0% or less by weight after up to about 2 weeks of storage, at a temperature up to about 60° C., and up to about 75% relative humidity.

5. The transdermal patch of claim 1, wherein at least one of the permeation enhancers is selected from diethylene glycol monoethyl ether, methyl laurate, polyoxyethylene(4) lauryl ether, and/or propylene glycol.

6. The transdermal patch of claim 1, wherein each acrylic-based polymer has pramipexole solubility between about 5% to about 10%.

7. The transdermal patch of claim 1, wherein the transdermal patch provides a flux rate of between about 9.3 µg/cm$^2$ hr and about 10 µg/cm2 hr.

8. A method for treating Parkinson's disease, restless leg syndrome, migraine headaches or ALS comprising the step of administering the transdermal patch of claim 1 to a human subject in need thereof, wherein the transdermal patch comprises a therapeutically effective amount of the pramipexole or its pharmaceutically acceptable salt thereof.

9. The method of claim 8, wherein the total delivered amount of pramipexole is from about 0.2 mg to about 10 mg daily.

\* \* \* \* \*